(12) United States Patent
Gupta et al.

(10) Patent No.: US 7,452,722 B2
(45) Date of Patent: Nov. 18, 2008

(54) METHODS FOR DEVELOPING CONIFER SOMATIC EMBRYOS

(75) Inventors: Pramod K. Gupta, Federal Way, WA (US); Diane G. Holmstrom, Sumner, WA (US); Bonnie Larson, Granite Falls, WA (US)

(73) Assignee: Weyerhaeuser Company, Federal Way, WA (US)

( * ) Notice: Subject to any disclaimer, the term of this patent is extended or adjusted under 35 U.S.C. 154(b) by 437 days.

(21) Appl. No.: 11/052,361

(22) Filed: Feb. 7, 2005

(65) Prior Publication Data

US 2005/0198713 A1 Sep. 8, 2005

Related U.S. Application Data

(60) Provisional application No. 60/549,396, filed on Mar. 2, 2004.

(51) Int. Cl.
*C12N 5/00* (2006.01)
*C12N 5/02* (2006.01)
(52) U.S. Cl. ............... 435/422; 435/430; 435/430.1
(58) Field of Classification Search ............... 435/422, 435/430, 430.1, 431
See application file for complete search history.

(56) References Cited

U.S. PATENT DOCUMENTS

| | | | |
|---|---|---|---|
| 4,217,730 A | 8/1980 | Abo El-Nil | |
| 4,801,545 A | 1/1989 | Stuart et al. | |
| 4,957,866 A | 9/1990 | Gupta et al. | |
| 5,034,326 A | 7/1991 | Pullman et al. | |
| 5,036,007 A | 7/1991 | Gupta et al. | |
| 5,041,382 A | 8/1991 | Gupta et al. | |
| 5,183,757 A | 2/1993 | Roberts | |
| 5,187,092 A | 2/1993 | Uddin | |
| 5,236,841 A | 8/1993 | Gupta et al. | |
| 5,238,835 A | 8/1993 | McKersie et al. | |
| 5,294,549 A | 3/1994 | Pullman et al. | |
| 5,413,930 A | 5/1995 | Becwar et al. | |
| 5,464,769 A | 11/1995 | Attree et al. | |
| 5,482,857 A | 1/1996 | Gupta et al. | |
| 5,491,090 A | 2/1996 | Handley, III et al. | |
| 5,491,091 A * | 2/1996 | Loshaek et al. ............ 436/1 |
| 5,501,972 A | 3/1996 | Westcott | |
| 5,506,136 A | 4/1996 | Becwar et al. | |
| 5,523,230 A | 6/1996 | Smith | |
| 5,534,433 A | 7/1996 | Coke | |
| 5,534,434 A | 7/1996 | Coke | |
| 5,563,061 A | 10/1996 | Gupta | |
| 5,564,224 A | 10/1996 | Carlson et al. | |
| 5,565,355 A | 10/1996 | Smith | |
| 5,587,312 A | 12/1996 | van Holst et al. | |
| 5,610,051 A | 3/1997 | Becwar et al. | |
| 5,677,185 A | 10/1997 | Handley, III | |
| 5,731,191 A | 3/1998 | Rutter et al. | |
| 5,731,203 A | 3/1998 | Handley, III | |
| 5,731,204 A | 3/1998 | Rutter et al. | |
| 5,821,126 A | 10/1998 | Durzan et al. | |
| 5,840,581 A | 11/1998 | Carraway et al. | |
| 5,850,032 A | 12/1998 | Wann | |
| 5,856,191 A | 1/1999 | Handley, III | |
| 5,985,667 A | 11/1999 | Attree et al. | |
| 6,022,744 A | 2/2000 | Tetteroo et al. | |
| 6,117,678 A | 9/2000 | Carpenter et al. | |
| 6,134,830 A | 10/2000 | Welty | |
| 6,150,167 A | 11/2000 | Carpenter et al. | |
| 6,180,405 B1 | 1/2001 | Aitken-Christie et al. | |
| 6,200,809 B1 | 3/2001 | Klimaszewska et al. | |
| 6,340,594 B1 | 1/2002 | Attree et al. | |
| 6,372,496 B1 | 4/2002 | Attree et al. | |
| 6,417,001 B2 | 7/2002 | Aitken-Christie et al. | |
| 6,444,467 B1 | 9/2002 | Fan et al. | |
| 6,492,174 B1 | 12/2002 | Pullman et al. | |
| 2002/0012994 A1 * | 1/2002 | Aitken-Christie et al. ... 435/422 |
| 2002/0092037 A1 | 7/2002 | Connett-Porceddu et al. | |
| 2002/0100083 A1 | 7/2002 | Connett-Porceddu et al. | |
| 2003/0022372 A1 * | 1/2003 | Aitken-Christie et al. ... 435/422 |

FOREIGN PATENT DOCUMENTS

| | | |
|---|---|---|
| EP | 0 300 730 B1 | 1/1989 |
| EP | 0 618 766 B1 | 10/1994 |
| EP | 0 934 691 A2 | 8/1999 |
| WO | WO 95/33822 A1 | 12/1995 |

(Continued)

OTHER PUBLICATIONS

Attree, S.M. et al., "Somatic Embryo Maturation, Germination, and Soil Establishment of Plants of Black and White Spruce (*Picea mariana* and *Picea glauca*)," *Can. J. Bot.* 68:2583-2589, 1990.

(Continued)

*Primary Examiner*—Wendy C. Haas
(74) *Attorney, Agent, or Firm*—Christensen O'Connor Johnson Kindness

(57) ABSTRACT

The present invention provides methods for producing conifer cotyledonary somatic embryos. The methods of the present invention each includes the step of culturing embryogenic conifer tissue in, or on, a development medium for a period of time sufficient to produce conifer cotyledonary somatic embryos from the embryogenic conifer tissue, wherein the volume of development medium is in the range of from about 35 ml to about 50 ml per 0.5 mL of embryogenic conifer tissue.

14 Claims, 1 Drawing Sheet

FOREIGN PATENT DOCUMENTS

| WO | WO 98/48279 A1 | 10/1998 |
|----|----------------|---------|
| WO | WO 99/46977 | 9/1999 |
| WO | WO 01/20972 A1 | 9/2000 |

OTHER PUBLICATIONS

Attree, S.M., et al., "Initiation of Embryogenic Callus and Suspension Cultures, and Improved Embryo Regeneration of Protoplasts, of White Spruce (*Picea glauca*)," *Can. J. Bot.* 67:1790-1795, 1989.

Attree, S.M., et al., "Plantlet Regeneration From Embryogenic Protoplasts of White Spruce (*Picea glauca*)," *Bio/Technology* 7:1060-1062, 1989.

Boulay, M.P., et al., "Development of Somatic Embryos From Cell Suspension Cultures of Norway Spruce (*Picea abies* Karst.)," *Plant Cell Reports* 7:134-137, 1988.

Cornu, D. and C. Geoffrion, "Aspects of Somatic Embryogenesis in Larch Trees," *Bull. Soc. Bot. Fr.*, 137 Actual. Bot. (3/4):25-34, 1990 [translation].

Garin E et al, "Effects of sugars, amino acids, and culture technique on maturation of somatic embryos of *Pinus strobes* on medium with two gellan gum concentrations," *Plant Cell Tiss & Org Cult* (62) 27-27, 2000.

Gupta, P.K., et al., "Scale-Up Somatic Embryogenesis of Conifers For Reforestation," Proceedings of the 3rd Canadian Workshop on Plant Tissue Culture and Genetic Engineering, University of Guelph, Symposium 1: Somatic Embryogenesis and Synthetic Seeds, Abstract, Jun. 1992.

Hakman, I. and L.C. Fowke, "An Embryogenic Cell Suspension Culture of *Picea glauca* (White Spruce)," *Plant Cell Reports* 6:20-22, 1987.

Jain, S.M., et al., Forestry Sciences: Somatic Embryogenesis in Woody Plants, vol. 3, Gymnosperms, Kluwer Academic Publishers, Netherlands, 1995.

Keinonen-Mettälä, K., et al., "Somatic Embryogenesis of *Pinus sylvestris*," *Scand. J. For. Res.* 11:242-250, 1996.

Klimaszewska K et al, "Maturation of somatic embryos of *Pinus strobes* is promoted by a high concentration of gellan gum," *Physiologica Plantarum* (100) 949-957, 1997.

Krogstrup, P. "Somatic Embryogenesis in Sitka Spruce (*Picea sitchensis*(Bong.) Carr.)," *Plant Cell Reports* 7:594-597, 1988.

Lelu Ma et al, "Somatic embryogenesis and plantlet development in *Pinus sylvestris* and *pinus pinaster* on median with and without growth regulators," *Phys Plantarum, Munksgaard Intl* (105) 719-718, 1999.

Lelu, M.A. et al., "Effect of Maturation Duration on Desiccation Tolerance in Hybrid Larch (*Larix X leptoeuropaea dengler*) Somatic Embryos," *In Vitro Cell. Dev. Biol.* 31:15-20, 1995.

Lu, C.-Y. and T.A. Thorpe, "Somatic Embryogenesis and Plantlet Regeneration in Cultured Immature Embryos of *Picea glauca*," *J. Plant Physiol.* 128:297-302, 1987.

Mathur, G. et al., "Studies on Somatic Embryogenesis From Immature Zygotic Embryos of CHIR Pine (*Pinus roxburghii* Sarg.)," *Current Science* 79(7):999-1004, 2000.

Norgaard, J.V., and P. Krogstrup, "Cytokinin Induced Somatic Embryogenesis From Immature Embryos of *Abies nordmanniana* Lk.," *Plant Cell Reports* 9:509-513, 1991.

Ramarosandtradana LH et al, "Effects of Carbohydrate Source, Polyethylene Glycol and Gellan Gum Concentration on Embryonal-Suspensor Mass (ESM) Proliferation and Maturation of Maritime Pine Somatic Embryos," *In vitro Cellular and Developmental Biology-Plant* 37:29-34.

Roberts, D.R., "Abscisic Acid and Mannitol Promote Early Development, Maturation and Storage Protein Accumulation in Somatic Embryos of Interior Spruce," *Physiologia Plantarum* 83:247-254, 1991.

Roberts, D.R et al., "Interaction Between Maturation and High Relative Humidity Treatments and Their Effects on Germination of Sitka Spruce Somatic Embryos," *J. Plant Physiol.* 138:1-6, 1991.

Roberts, D.R., et al., "Synchronous and High Frequency Germination of Interior Spruce Somatic Embryos Following Partial Drying at High Relative Humidity," *Can. J. Bot.* 68:1086-1090, 1989.

Taber RP et al., "Kinetics of Douglas-fir (*Pseudotsungo menziesii*) somatic embryo development," *Can J Bot* (76): 838-871, 1998.

Thompson, R.G. and P. von Aderkas, "Somatic Embryogenesis and Plant Regeneration From Mature Embryos of Western Larch," *Plant Cell Reports* 11:379-386, 1992.

Timmis, R., "Bioprocessing for Tree Production in the Forest Industry: Conifer Somatic Embryogenesis," *Biotechnol. Prog.* 14(1):156-166, 1998.

Von Aderkas, P., et al., "Charcoal Affects Early Development and Hormonal Concentrations of Somatic Embryos of Hybrid Larch," *Tree Physiology* 22:431-434, 2002.

Von Arnold, S. and I. Hakman, "Regulation of Somatic Embryo Development in *Picea abies* by Abscisic Acid (ABA)," *J. Plant Physiol.* 132:164-169, 1988.

Von Arnold, S. and T. Eriksson, "A Revised Medium for Growth of Pea Mesophyll Protoplasts," *Physiol. Plant* 39:257-260, 1977.

Webb, D.T., et al., "Factors Influencing the Induction of Embryogenic and Caulogenic Callus From Embros of *Picea glauca* and *P. engelmanii*," *Can. J. For. Res.* 19:1303-1308, 1989.

\* cited by examiner

METHODS FOR DEVELOPING CONIFER SOMATIC EMBRYOS

CROSS REFERENCE TO RELATED APPLICATION

The present application claims the benefit of U.S. Provisional Application No. 60/549,396, filed Mar. 2, 2004.

FIELD OF THE INVENTION

The present invention relates to methods for producing plant embryos in vitro and optionally producing plants from the plant embryos.

BACKGROUND OF THE INVENTION

The demand for conifer trees (e.g., pines and firs) to make wood products continues to increase. One proposed solution to this problem is to identify individual trees that possess desirable characteristics, such as a rapid rate of growth, and produce numerous, genetically identical clones of the superior trees by somatic cloning. Somatic cloning is the process of producing plant embryos, in vitro, from plant cells that are not zygotes. These clones can be cultivated to yield stands, or whole forests, of conifer trees that possess the desirable characteristic(s).

One method for somatically cloning trees utilizes in vitro treatment of isolated, living, conifer tissue under conditions that promote formation of conifer somatic embryos, and then whole plants, from the treated tissue. The isolated conifer tissue may be cultured in the presence of one or more auxins, and/or cytokinins, to promote formation and multiplication of embryogenic tissue that is then cultured under conditions that promote formation of cotyledonary embryos that are morphologically similar to zygotic embryos produced in vivo. The embryos may then be germinated to yield conifer trees. An example of conifer embryogenic tissue are embryonal suspensor masses (ESMs) that can be formed, by tissue culture in vitro, from conifer embryos dissected from conifer seeds. By way of example, FIG. 1 shows pine embryonal suspensor masses in liquid culture. FIG. 2 shows a pine, cotyledonary, somatic embryo formed from ESM (cotyledons are visible at the top of the embryo).

A continuing problem, however, is stimulating efficient formation of conifer, cotyledonar, somatic embryos that are capable of germinating with high frequency to yield conifer plants. Preferably, the conifer cotyledonary somatic embryos, formed in vitro, are morphologically, anatomically and biochemically similar, or identical, to zygotic conifer embryos formed, in vivo, in conifer seeds of the same species. In particular, there is a need for methods for producing, in vitro, greater numbers of zygotic-like cotyledonary somatic embryos than are produced by prior art methods. Preferably, the germination frequency and quality of the conifer, cotyledonary, somatic embryos produced by the novel methods should be higher than the germination frequency and quality of conifer cotyledonary somatic embryos produced by prior art methods.

SUMMARY OF THE INVENTION

In accordance with the foregoing, the present invention provides methods for producing conifer cotyledonary somatic embryos. The methods of the present invention each includes the step of culturing conifer embryogenic tissue in, or on, a development medium for a period of time sufficient to produce conifer cotyledonary somatic embryos from the embryogenic conifer tissue, wherein the volume of development medium is in the range of from about 35 ml to about 50 ml per 0.5 mL of embryogenic conifer tissue.

The methods of the invention are useful, for example, for producing conifer cotyledonary somatic embryos from any conifer plant species. The somatic embryos can be germinated and grown to produce trees. The present inventors have found that the methods of the invention produce more conifer cotyledonary somatic embryos than identical methods that use less than from about 35 ml to about 50 ml per 0.5 mL of conifer embryogenic tissue.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
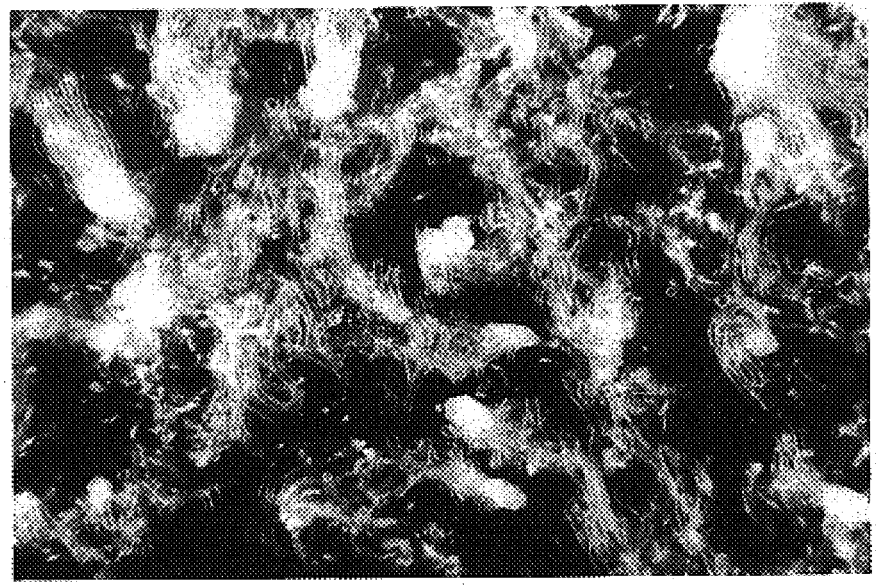
FIG. 1 shows pine embryonal suspensor masses in liquid culture.
Figure 2:
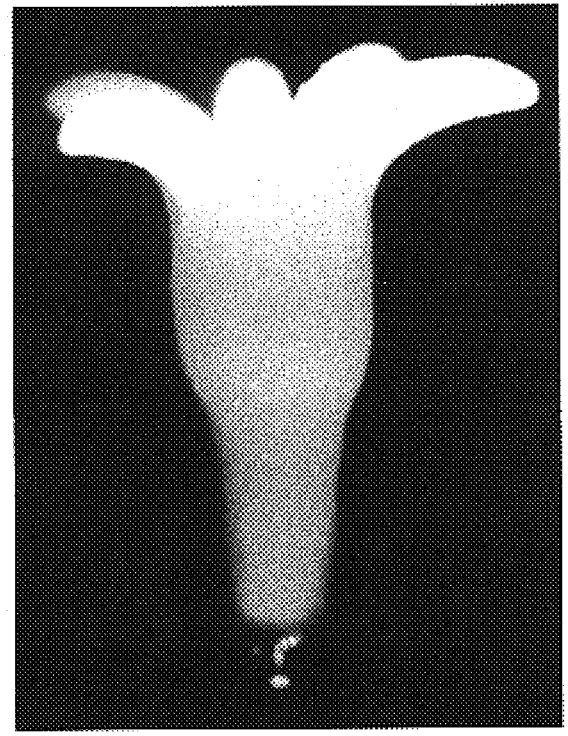
FIG. 2 shows a pine cotyledonary somatic embryo formed from ESM (cotyledons are visible at the top of the embryo).

Unless specifically defined herein, all terms used herein have the same meaning as they would to one skilled in the art of the present invention.

As used herein, the term "cotyledonary embryo" means an embryo that possesses one or more cotyledons.

As used herein, the term "somatic embryo" refers to a plant embryo that developed in vitro from a plant cell, or tissue, that is not a zygote.

As used herein, the term "embryogenic tissue" refers to any tissue, derived from a conifer, which is capable of producing one or more conifer cotyledonary somatic embryos when treated in accordance with the methods of the invention. Thus, the term "embryogenic tissue" includes, for example, conifer embryonal suspensor masses.

Unless stated otherwise, all concentration values that are expressed as percentages are weight per volume percentages.

The present invention provides methods for producing conifer cotyledonary somatic embryos. The methods each includes the step of culturing conifer embryogenic tissue in, or on, a development medium for a period of time sufficient to produce conifer cotyledonary somatic embryos from the conifer embryogenic tissue, wherein the volume of development medium is in the range of from about 35 ml to about 50 ml per 0.5 mL of embryogenic tissue. In some embodiments of the methods of the invention, the volume of development medium is in the range of from 40 ml to about 50 ml per 0.5 mL of embryogenic conifer tissue. The methods of the present invention can be used to produce cotyledonary somatic embryos from any conifer species, such as members of the family Pinacea, including members of the genus *Pinus* (e.g., Loblolly pine (*Pinus taeda*)), or such as members of the genus *Pseudotsuga* (e.g., Douglas fir (*Pseudotsuga menziesii*)).

An example of embryogenic tissue useful in the practice of the present invention is embryonal suspensor masses (ESMs). ESMs can be prepared from precotyledonary embryos removed from conifer seed. The seed are typically surface sterilized before removing the precotyledonary embryos, which are then cultured on, or in, medium that permits formation of ESMs that include early stage embryos in the process of multiplication by budding and cleavage. The medium may, if desired, include hormones that stimulate multiplication of the early stage embryos. Examples of hormones that can be included in the medium are auxins (e.g., 2,4-dichlorophenoxyacetic acid (2,4-D)) and cytokinins (e.g., 6-benzylaminopurine (BAP)). Auxins can be utilized, for example, at a concentration of from 1 mg/L to 200 mg/L. Cytokinins can be utilized, for example, at a concentration of from 0.1 mg/L to 50 mg/L. An example of a medium useful for culturing Loblolly pine precotyledonary embryos to induce formation of ESMs is medium $LM_1$ set forth in Example 2 herein. An example of a medium useful for culturing Douglas fir precotyledonary embryos to induce formation of ESMs is medium $DM_1$, set forth in Example 3 herein.

In the practice of the present invention, conifer embryogenic tissue is cultured in, or on, a development medium for a period of time sufficient to produce conifer cotyledonary somatic embryos from the conifer embryogenic tissue. The development medium is formulated to promote development of conifer cotyledonary somatic embryos from conifer embryogenic tissue. The development medium may be a solid medium or a liquid medium. When a liquid development medium is used, the embryogenic tissue may be completely immersed in the medium, which may be agitated during the time that the embryogenic tissue is cultured therein. An absorbent substrate (e.g., a pad made from cellulose, or some other material that absorbs aqueous solutions, such as a development medium) may be soaked in liquid development medium, and the conifer somatic embryos disposed on the soaked pads and in contact with the development medium.

When a solid medium is used, the embryogenic tissue may be placed on the surface of the development medium, and may partially penetrate the surface of the solid medium. Thus, solid development media include media that are partially solidified and permit the embryogenic tissue to substantially penetrate into the body of the medium, and also include fully solidified media that do not permit the embryogenic tissue to penetrate the body of the solidified medium. Liquid media can be completely or partially solidified by addition of an appropriate amount of a gellant, such as agar.

The development medium contains nutrients that sustain the embryogenic tissue. Maltose may be included in the medium as the principal or sole source of metabolizable sugar for the embryogenic tissue. Examples of useful maltose concentrations are within the range of from 2.5% to 6.0%. Suitable development media typically do not include growth-promoting hormones, such as auxins and cytokinins, but may include the hormone abscisic acid. When abscisic acid is utilized in the development medium, it is typically used at a concentration in the range of from 1 mg/L to 200 mg/L, such as from 1 mg/L to 100 mg/L. The osmolality of the development medium can be adjusted to a value that falls within a desired range, such as from 250 mM/Kg to 450 mM/Kg, or such as from 250 mM/Kg to 350 mM/Kg. The pH of the development medium may also be adjusted to a value within a desired range, such as from 4.5 to 6.5, or such as from 5.0 to 6.0. The embryogenic tissue is typically incubated in, or on, the development medium at a temperature in the range of from 20° C. to 24° C., such as from 21° C. to 24° C. An example of a suitable Loblolly pine development medium is medium $LM_5$ set forth in Example 2 herein. An example of a suitable Douglas fir development medium is medium $DM_4$ set forth in Example 3 herein.

Embryogenic conifer tissue is cultured in, or on, a development medium for a period of time sufficient to produce cotyledonary conifer somatic embryos from the embryogenic conifer tissue. For example, Douglas fir embryonal suspensor masses are typically cultured in, or on, development medium for from about seven weeks to about eight weeks to produce Douglas fir cotyledonary somatic embryos. Again by way of example, Loblolly pine embryonal suspensor masses are typically cultured in, or on, development medium for from about ten weeks to about 12 weeks to produce Loblolly pine cotyledonary somatic embryos.

In the practice of the present invention, the volume of development medium is in the range of from about 35 ml to about 50 ml per 0.5 mL of embryogenic conifer tissue. The term "about" as used in this context includes the exact range of ratios (e.g., the range "about 35 ml to about 50 ml" includes the range of 35 ml to 50 ml). The volume of conifer embryogenic tissue can be measured by placing a culture vessel including a liquid culture of conifer embryogenic tissue on a horizontal surface (e.g., laboratory bench) for 30 minutes at room temperature (typically in the range of 20° C. to 25° C.). The tissue settles to the bottom of the culture vessel and the volume of settled tissue is measured (e.g., by drawing the settled tissue up into a calibrated pipette, or by looking at the level of the settled tissue in relation to volume calibration marks on the culture vessel). The tissue volume measured in this way is referred to as the settled cell volume (abbreviated as SCV).

The present inventors have found that using from about 35 ml to about 50 ml per 0.5 mL of embryogenic conifer tissue promotes the growth and development of conifer cotyledonary somatic embryos from conifer embryogenic tissue. When a development medium is used that includes abscisic acid present at a concentration of from about 1 mg/L to 200 mg/L, culturing conifer embryogenic tissue in, or on, more than about 50 ml development medium per 0.5 mL of conifer embryogenic tissue provides the developing tissue with too much abscisic acid which may retard development. Moreover, developing cotyledonary somatic embryos metabolize sugar in the development medium, and so reduce the osmotic potential of the medium over time, thereby maintaining the osmotic potential within an acceptable range. If too much sugar is present in the development medium then the embryos cannot metabolize a sufficient amount to maintain the osmotic potential of the medium at an acceptable level over time. Thus, in the practice of the present invention, the volume of development medium provides sufficient sugar, and other nutrients, to enhance embryo growth and development, without providing so much sugar that the osmotic potential of the medium is too high.

In some embodiments, the present invention provides methods for producing Douglas fir cotyledonary somatic embryos or Loblolly pine cotyledonary somatic embryos, wherein these methods include the steps of (a) culturing Douglas fir zygotic embryos, or Loblolly pine zygotic embryos, in, or on, an initiation medium for a period of time sufficient to produce embryonal suspensor masses; (b) culturing the embryonal suspensor masses in, or on, a maintenance medium under conditions effective to promote multiplication of the embryonal suspensor masses; and (c) culturing the multiplied embryonal suspensor masses in, or on, a development medium for a period of time sufficient to produce Douglas fir, or Loblolly pine, cotyledonary somatic embryos from the embryonal suspensor masses, wherein the volume of development medium is in the range of from about 35 ml to about 50 ml per 0.5 mL of embryogenic conifer tissue. In some embodiments of the methods of the invention, the volume of development medium is in the range of from about 40 ml to about 50 ml per 0.5 mL of embryogenic conifer tissue.

The initiation medium typically includes inorganic salts and organic nutrient materials. The osmolality of the initiation medium is typically about 160 mg/kg or even lower, but it may be as high as 170 mM/kg. The initiation medium typically includes growth hormones. Examples of hormones that can be included in the initiation medium are auxins (e.g., 2,4-dichlorophenoxyacetic acid (2,4-D)) and cytokinins (e.g., 6-benzylaminopurine (BAP)). Auxins can be utilized, for example, at a concentration of from 1 mg/L to 200 mg/L. Cytokinins can be utilized, for example, at a concentration of from 0.1 mg/L to 50 mg/L.

The initiation medium may contain an adsorbent composition, especially when very high levels of growth hormones are used. The adsorbent composition can be any composition that is not toxic to the embryogenic cells at the concentrations utilized in the practice of the present methods, and that is capable of adsorbing growth-promoting hormones, and toxic compounds produced by the plant cells during pre-cotyledonary embryo development, that are present in the medium. Non-limiting examples of useful adsorbent compositions include activated charcoal, soluble poly(vinyl pyrrolidone), insoluble poly(vinyl pyrrolidone), activated alumina, and silica gel. The adsorbent composition may be present in an amount, for example, of from about 0.1 g/L to about 5 g/L. An example of a Loblolly pine initiation medium is medium $LM_1$ set forth in Example 2 herein. An example of a Douglas fir initiation medium is medium $DM_1$ set forth in Example 3 herein.

Conifer somatic cells are typically cultured in, or on, an initiation medium for a period of from 6 weeks to 12 weeks, such as 8 weeks to 10 weeks, or such as about 8 weeks, at a temperature of from 10° C. to 30° C., such as from 15° C. to 25° C., or such as from 20° C. to 23° C.

The maintenance medium is formulated to promote the growth and multiplication of conifer embryogenic tissue, such as embryonal suspensor masses. The maintenance medium may be a solid medium, or it may be a liquid medium which, for example, can be agitated to promote growth and multiplication of the embryogenic tissue. The osmolality of the maintenance medium is typically higher than the osmolality of the initiation medium, typically in the range of 180-400 mM/kg. The maintenance medium may contain nutrients that sustain the embryogenic tissue, and may include hormones, such as one or more auxins and/or cytokinins, that promote cell division and growth of the embryogenic tissue. Typically, the concentrations of hormones in the maintenance medium is lower than their concentration in the initiation medium.

It is generally desirable, though not essential, to include maltose as the sole, or principal, metabolizable sugar source in the maintenance medium. Examples of useful maltose concentrations are within the range of from about 2.5% to about 6.0%. An example of a suitable Loblolly pine maintenance medium is medium $LM_2$ set forth in Example 2 herein. An example of a suitable Douglas fir maintenance medium is medium $DM_2$ set forth in Example 3 herein. Conifer embryogenic tissue is typically cultured in, or on, a maintenance medium for a period of up to 6 months by weekly subculture, at a temperature of from 10° C. to 30° C., such as from 15° C. to 25° C., or such as from 20° C. to 23° C.

The embryogenic tissue is then transferred from the maintenance medium to a development medium formulated to promote development of conifer cotyledonary somatic embryos from the conifer embryogenic tissue. The composition and characteristics of suitable development media are described supra.

The conifer cotyledonary somatic embryos produced using the methods of the invention can optionally be germinated to form conifer plants which can be grown into conifer trees, if desired. The germinated plants can be transferred to soil for further growth. For example, the germinated plants can be planted in soil in a greenhouse and allowed to grow before being transplanted to an outdoor site. Typically, the conifer cotyledonary somatic embryos are illuminated to stimulate germination. Typically, all the steps of the methods of the invention, except germination, are conducted in the dark.

The conifer cotyledonary somatic embryos produced using the methods of the invention can also be introduced into manufactured seeds which may be stored for subsequent planting and germination, or which may be planted without a period of storage. Representative examples of useful manufactured seeds include the manufactured seeds disclosed in U.S. Pat. No. 5,687,504, which is incorporated by reference herein in its entirety.

The methods of the invention can be used, for example, to produce clones of individual conifer trees that possess one or more desirable characteristics, such as a rapid growth rate. Thus, in one aspect, the present invention provides methods for producing a population of genetically identical, conifer, cotyledonary somatic embryos, wherein any of the methods described herein is used to produce a population of genetically identical, cotyledonary somatic embryos from a genetically homogeneous starting material (e.g., from a single Loblolly pine or Douglas fir zygotic embryo).

The following examples merely illustrate the best mode now contemplated for practicing the invention, but should not be construed to limit the invention.

EXAMPLE 1

This Example describes the results of an experiment that shows that increasing the ratio of the volume of solid development medium to the mass of Loblolly pine ESMs increases the number of good quality, cotyledonary, somatic embryos that develop from the ESMs.

Loblolly pine ESMs were plated onto solid development medium. The composition of the development medium was the same as medium LM4 (described in Example 2) except that the concentration of maltose was 20 g/L, there was no glucose present in the medium, the concentration of polyethylene glycol was 130 g/L, and the concentrations of $FeSO_4$ and $Na_2EDTA$ were half the respective concentrations in medium LM4.

ESMs from four Loblolly pine genotypes were used—Genotype LP-A, Genotype LP-B, Genotype LP-C., and Genotype LP-D. Approximately 0.5 mL ESMs from each of the four Loblolly pine genotypes were plated onto either 10 ml or 42 ml of solid development medium in Petri dishes. There were 10 plates×2 treatments×4 genotypes=80 plates.

Observations regarding embryo quality were made at 4, 8, and 10 weeks after plating onto development medium. Quality assessments included color, size and shape of embryos as well as the condition of underlying ESM. The fourth week observations were cursory only, to identify any major developmental differences that occurred. By the eighth week, assessment was more thorough. All genotypes were producing cotyledonary embryos on both treatments.

After 10 weeks, quality was much the same as at 8 weeks, but all embryos were a little further developed. Genotype LP-A was the most developed, with embryos on solid media being very green and reflexed at the cotyledons. Genotype LP-B was next most developed, with "C" and "D" lagging behind.

Table 1 shows the average cotyledonary somatic embryo yields for each genotype, and the yields for all genotypes considered together for each treatment. Overall, the larger development medium volume produced higher yields of good quality embryos.

TABLE 1

| Treatment | All Genos | | Geno A | | Geno B | | Geno C | | Geno D | |
|---|---|---|---|---|---|---|---|---|---|---|
| | Yield | SE | Yield | SE | Yield | SE | Yield | SE | Yield | SE |
| 10-ml small | 14 | 2.0 | 29 | 3.3 | 19 | 1.8 | 4 | 1.0 | 2 | 0.7 |
| 42-ml large | 41 | 6.2 | 104 | 7.7 | 31 | 3.3 | 21 | 2.8 | 19 | 2.9 |

EXAMPLE 2

This example describes a representative method of the present invention for producing Loblolly pine cotyledonary somatic embryos.

TABLE 2

LOBLOLLY PINE BASAL CULTURE MEDIUM (LM)

| Basal Salts | mg/L | Basal Salts | mg/L |
|---|---|---|---|
| $NH_4NO_3$ | 150 | $H_3BO_3$ | 15.5 |
| $KNO_3$ | 909.9 | $MnSO_4.H_2O$ | 10.5 |
| $Ca(NO_3)_2.4H_2O$ | 236.2 | $ZnSO_4.7H_2O$ | 14.4 |
| $MgSO_4.7H_2O$ | 246.5 | $NaMoO_4.2H_2O$ | 0.125 |
| $Mg(NO_3)_2.6H_2O$ | 256.5 | $CuSO_4.5H_2O$ | 0.125 |
| $MgCl_2.6H_2O$ | 50 | $CoCl_26H_2O$ | 0.125 |
| $KH_2PO_4$ | 136 | $FeSO_4.7H_2O$ | 27.85 |
| $CaCl_2.2H_2O$ | 50 | $Na_2EDTA$ | 37.25 |
| KI | 4.15 | | |

| Organic Additives | mg/L | Organic Additives | mg/L |
|---|---|---|---|
| Nicotinic acid | 0.5 | Casamino acids | 500 |
| Pyridoxine.HCl | 0.5 | L-Glutamine* | varies |
| Thiamine.HCl | 1 | Myo-Inositol | varies |
| Glycine | 2 | Carbohydrate | varies |
| pH | 5.7 | | |

*L-Glutamine is filter sterilized in maintenance media for some genotypes.

TABLE 3

FORMULATIONS OF LOBLOLLY PINE MEDIA

| (All units are in mg/L) | LM-1 Stage I Initiation | LM-2 Stage II Maintenance | LM-3 Rinse | LM-4 Stage III Solid Develpmt | LM-5 Stage III Liquid Develpmt | LM-6* Stage IV Stratification |
|---|---|---|---|---|---|---|
| L-Proline | — | — | 100 | 100 | 100 | 100 |
| L-Asparagine | — | — | 100 | 100 | 100 | 100 |
| L-Arginine | — | — | 50 | 50 | 50 | 50 |
| L-Alanine | — | — | 20 | 20 | 20 | 20 |
| L-Serine | — | — | 20 | 20 | 20 | 20 |
| L-glutamine | 250 | 1000 | 1000 | 1000 | 1000 | 1000 |
| Myo-Inositol | 200 | 200 | 1000 | 1000 | 1000 | 1000 |
| Maltose | 30,000 | 30,000 | 25,000 | 25,000 | 25,000 | 25,000 |
| Glucose | — | — | — | 10,000 | 10,000 | — |
| PEG 8000 | — | — | — | 100,000 | 120,000 | — |
| Activated charcoal | 1250 | — | — | 1000 | 1000 | 1000 |
| Gelrite | 1600 | 1600** | — | 2500 | — | — |
| 2.4-D | 55 | 1.1 | — | — | — | — |
| BAP | 7.5 | 0.1 | — | — | — | — |
| Kinetin | 7.5 | 0.1 | — | — | — | — |
| ABA | — | +/−1.0*** | 10 | 25 | 25 | — |

*LM-6 Stratification medium has only half the basal amounts of FeSO4.7H2O (13.93 mg/L) and Na2EDTA (18.83 mg/L).
**Gelrite not used for liquid media.
***ABA is added on a per-genotype basis. Some genotypes have been found to do better with ABA in maintenance. The pH of all media are adjusted to 5.7.

The composition of the basal tissue culture medium is set forth in Table 2. The modifications to the basal medium composition that are required for each culture medium are listed in Table 3. Each tissue culture medium is prepared by mixing together all the ingredients, with the exception of abscisic acid and maltose (if needed), and bringing the medium to the desired volume prior to autoclaving (15 minutes at 121° C., 15 psi). The abscisic acid is filter-sterilized and aseptically added to the sterile medium. L-glutamine is also filter-sterilized prior to addition to maintenance medium. In media requiring maltose, the medium is made up to 90% of the required volume. A 10× stock solution of maltose is autoclaved, or filter-sterilized, and added to the autoclaved medium. Gelrite is added to make solid LM-1 and LM-2 medium. Ten ml of LM-1 or LM-2 medium is poured into 60×15 mm plates, or 20 ml of LM-1 or LM-2 medium is poured into 100×25 mm plates.

Initiation of Embryogenic Cultures: Female cones are collected when immature embryos reach pre-dome or dome stage in development. Collection usually begins in the first week of July (about 4-6 weeks after fertilization), and continues until the first appearance of cotyledon primordia (middle of July). The optimal embryo stage for initiation is when the apical dome begins to develop.

The seeds are removed from the cones and are immersed in a 10% solution of Liquinox that includes a few drops of Tween-20 detergent, and agitated for 10 minutes. The seeds are then rinsed with distilled water for 30 minutes. The seeds are agitated in a 15% (v/v) solution of $H_2O_2$ for 10 minutes. The seeds are then washed five times by agitating in successive aliquots of sterile water in a laminar-flow hood.

The surface-sterilized seeds are then transferred to a petri plate, and the seeds are viewed under a dissecting microscope, and the seed coat and nucellar membrane are removed with scalpel and forceps. The excised female gametophyte is placed onto LM-1 induction medium. The excised gametophyte should be placed so that its longitudinal axis is parallel to the media surface, and so that the micropyle is in contact with, but not submerged in, the culture medium. The plates are sealed with a double layer of parafilm and the cultures are incubated in the dark at 23° C.

After 2-3 weeks, extrusion of somatic embryos occurs from the micropylar end of the female gametophyte. A mucilaginous, translucent-white mass develops (0.5-10 mm) around the heads of these immature embryos. This is called an embryonal suspensor mass (ESM). An embryonal suspensor mass is made up of embryos at various early stages of development. Each embryo contains an embryonal head and suspensor system.

Maintenance of Embryonal Suspensor Masses: Five to six weeks after placing the excised female gametophytes on LM-1 induction medium, the ESM is separated from the original explants and transferred onto solid maintenance medium (LM-2). ESM cultures multiply by natural conifer-type cleavage polyembryony. ESM cultures are subcultured every two weeks onto fresh medium and incubated in the dark at 23° C. The ESM cultures are divided into two pieces when they reach 1 cm long, and all the pieces are maintained until there are several which can be used to start a suspension culture.

Establishing Suspension Cultures: One to two grams (fresh weight) ESM (four or five 1-cm pieces) are transferred into a 250 ml Erlenmeyer flask containing 20 ml of LM-2 liquid medium. The flask is placed on a rotary shaker (90-110 rpm) in darkness at 23° C. After one week the settled cell volume (SCV) is measured, and if the SCV is less than 3 ml, the flask is returned to the shaker without making any additions or changes to the medium. If the SCV is at least 5 ml, 25 ml of fresh medium are added to the flask that is returned to the shaker.

After the second week, the cultures are settled for 15 minutes on a tilted flask holder. If the flask did not have medium added the week before, 10 ml of spent media are removed and replaced with 10 ml of fresh medium. If medium was added to the flask in the previous week, and the culture appears to be growing vigorously, the culture is transferred as described below.

When cultures are sufficiently established to produce 10 ml, or more, of settled cells per week, the ESM is maintained by regular weekly subculture. Subculturing is achieved by settling the cultures for 15 minutes, aspirating the supernatant, and measuring 10 ml of ESM into a flask containing 45 ml of fresh LM-2 maintenance medium. ESM is subcultured at a ratio of 1:4 cells to medium (v/v). If a larger volume of cells is desired, the ESM is split into additional flasks over several weeks, until enough cells are available to use a larger flask. Cultures at this stage may be cryostored, or they may be singulated and developed for germination.

Embryo Development: Embryo development is completed using a liquid development medium, LM-5, that is soaked into a double layer of Concert 10% CC pads in a petri dish or Cambro box. The cultures are settled after culture in maintenance medium, and aspirated to remove the supernatant. The settled cell volume is measured with a pipette during transfer to a cytostir beaker. A volume of rinse medium (LM-3), equal to the settled cell volume, is added to the settled cells. The cells in LM-3 medium are swirled in the cytostir beaker, and settled for an additional 10 minutes. Half the supernatant is removed, and the remaining ESM are transferred to a cytostir beaker. The cells are stirred on a stir plate.

The ESM is pipetted onto a filter paper that is located on a pad soaked in liquid development medium. The volume of ESM pipetted onto the filter paper depends on the mass of ESMs, and is sufficient to provide at least about 35 ml development medium per half milliliter of ESM. 0.75 ml ESM mixture (approximately 100 mg ESMs) are used per standard 2"×2" pad. The plates are sealed with two layers of parafilm, and incubated in the dark at 23° C. After about 12 weeks, the ESM cultures produce cotyledonary embryos.

Stratification: Stratification is the process of placing embryos in a cold moist environment for several weeks, which is thought to simulate winter.

Plates are prepared that include a single layer of pad material (2"×2: 10% CC., or larger cut to fit Cambro boxes). About 18-19 ml liquid LM-6 media are added per 2"×2: pad (more for boxes). A filter paper bearing the Loblolly pine embryos is transferred from development plates to pads of stratification medium. Alternatively, zygotic-like cotyledonary embryos may be selected from the development medium and placed onto new filter papers on stratification medium. Plates are sealed with parafilm and placed in the dark at 2-6° C. for four weeks.

Conditioning Somatic Embryos: In addition to stratification, a post-development "conditioning" treatment, in which embryos are exposed to a high relative humidity (RH) environment, improves germination. The high RH environment is provided by the addition of sterile water to a half-Cambro box. Embryos are singulated after stratification and placed onto dry filter papers in a large petri plate. The open plate is placed in the half-Cambro box containing sterile water. The embryos are exposed to the high RH environment until the moisture contents of the embryos reach 60-65%. The boxes are closed so that the gaskets seal tightly, and are clipped shut with binder clips before being placed in the dark for 3 weeks at 23° C. After conditioning, the mature somatic embryos are removed from the boxes and can be inserted into manufactured seed for subsequent germination and seedling establishment, or can be directly germinated.

EXAMPLE 3

This Example describes a representative method of the present invention for producing Douglas fir (*Pseudotsuga menziesii*) cotyledonary somatic embryos.

The composition of basal medium is listed in Table 4. Modifications of the basal medium required for each culture medium are listed in Table 5. The composition of stratification medium is set forth in Table 6. The concentration units in Tables 4, 5, and 6 are milligrams per liter (mg/L). The media are prepared by mixing together all of the ingredients, with the exception of abscisic acid (ABA), gibberellic acid (GA) and maltose (if needed), and bringing the media to the desired volume prior to autoclaving for 15 minutes at 121° C., 15 psi. ABA and GA 4/7 are filter-sterilized and aseptically added to sterile media. If the medium requires maltose, the medium is first brought to 90% of the desired volume, and an aliquot of a sterile, 10×, stock solution of maltose is added to the autoclaved media. Gelrite is used to make solid DM-1 plates, and tissue culture (TC) agar to make solid DM-2 plates. Ten ml/plate of DM-1 or DM-2 medium is added to 60×15 mm plates, or 20 ml/plate of DM-1 or DM-2 medium is added to 100×25 mm plates.

TABLE 4

DOUGLAS FIR BASIC CULTURE MEDIA (DM)

| Basal Salts | mg/L | Organic Additives | mg/L |
|---|---|---|---|
| $KNO_3$ | varies | Myo-Inositol | varies |
| $CaCl_2.2H_2O$ | 200 | Thiamine.HCl | 1 |
| $Ca(NO_3)_2.4H_2O$ | varies | Nicotinic acid | 0.5 |
| $KH_2PO_4$ | 340 | Pyridoxine.HCl | 0.5 |
| $MgSO_4.7H_2O$ | 400 | Glycine | 2 |
| $MnSO_4.H_2O$ | 15.8 | L-Glutamine | varies |
| $ZnSO_4.7H_2O$ | 8 | Casamino acids | 500 |
| $CuSO_4.5H_2O$ | 0.024 | Sucrose or Maltose | varies |
| $FeSO_4.7H_2O$ | 27.85 | | |
| $Na_2EDTA$ | 37.25 | pH | 5.7 |
| $H_3BO_3$ | 5 | | |
| $NaMoO_4.2H_2O$ | 0.2 | | |
| $CoCl_2.6H_2O$ | 0.02 | | |
| KI | 1 | | |

TABLE 5

FORMULATIONS OF DOUGLAS FIR MEDIA

| | DM-1 Stage I Initiation | DM-2 Stage II Maintenance | DM-3 Stage III Singulation | DM-4 Stage IV Development |
|---|---|---|---|---|
| $KNO_3$ | 1250(1) | 1250 | 1050 | 2500 |
| $Ca(NO_3)_2.4H_2O$ | — | — | 200 | — |
| Myo-Inositol | 1000 | 5000 | 100 | 100 |
| L-Glutamine | 450 | 1000 | 1000 | 750 |
| Amino acid mixture(2) | — | — | — | 290 |
| Maltose | — | 30,000 | 20,000 | 25,000 |
| Sucrose | 15,000 | — | — | — |
| PEG 8000 | — | — | — | 190,000 |
| 2.4-D | 110 | 1.1 | — | — |
| N6-Benzyl-adenine (BAP) | 45 | 0.22 | — | — |
| Kinetin | 43 | 0.22 | — | — |
| Abscisic acid | — | — | 10/5/5 | 10 |
| Gibberellic acid | — | — | — | 7.5 |
| Activated charcoal | 2500 | — | — | 1000 |
| Tissue culture agar | — | 5000(3) | — | — |
| Gelrite | 1800 | — | — | — |

(1)All units are in mg/L (or ppm)
(2)L-Proline - 100, L-Asparagine - 100, L-Arginine - 50, L-Alanine - 20, L-Serine - 20
(3)Tissue culture agar not used for liquid media
The pH of all media are adjusted to 5.7

TABLE 6

STRATIFICATION MEDIUM (SM)

| Basal Salts | mg/L | Organic Additives | mg/L |
|---|---|---|---|
| $NH_4NO_3$ | 206.3 | Myo-Inositol | 100 |
| $KNO_3$ | 1170 | Thiamine.HCl | 1 |
| $CaCl_2.2H_2O$ | 220 | Nicotinic acid | 0.5 |
| $Ca(NO_3)_2.4H_2O$ | none | Pyridoxine.HCl | 0.5 |
| $KH_2PO_4$ | 85 | Glycine | 2 |
| $MgSO_4.7H_2O$ | 185 | Casamino acids | none |
| $MnSO_4.H_2O$ | 8.45 | Sucrose | 20,000 |
| $ZnSO_4.7H_2O$ | 4.3 | | |
| $CuSO_4.5H_2O$ | 0.013 | Activated charcoal | 2500 |
| $FeSO_4.7H_2O$ | 13.93 | | |
| $Na_2EDTA$ | 18.63 | | |
| $H_3BO_3$ | 3.1 | pH | 5.7 |
| $NaMoO_4.2H_2O$ | 0.125 | | |
| $CoCl_2.6H_2O$ | 0.013 | | |
| KI | 0.42 | | |

Initiation of Embryogenic Cultures: Female cones are collected when immature embryos reach pre-dome and dome stage in development. Collections usually begin in the first week of July (about 4-6 weeks after fertilization) until the first appearance of cotyledon primordia (middle of July). The optimal embryo stage for initiation is when the apical dome begins to develop, but prior to formation of cotyledons.

The seeds are removed from the cones and are immersed in a 10% solution of Liquinox that includes a few drops of Tween-20 detergent, and agitated for 10 minutes. The seeds are then rinsed with distilled water for 30 minutes. The seeds are agitated in a 20% (v/v) solution of $H_2O_2$ for 10 minutes. The seeds are then washed five times by agitating in successive aliquots of sterile water in a laminar-flow hood.

The surface-sterilized seeds are then transferred to a petri plate, and the seeds are viewed under a dissecting microscope, and the embryos are excised so that they remain attached to the female gametophyte. The excised female gametophyte is placed onto DM-1 induction medium so that the embryos are touching the medium. The plates are wrapped with a double layer of parafilm and the cultures are incubated in the dark at 23° C.

After 5-9 weeks, extrusion of somatic embryos occurs from the micropylar end of the female gametophyte. A mucilaginous, translucent-white mass develops (0.5-10 mm) around the heads of these immature embryos. This is called an embryonal suspensor mass (ESM). An embryonal suspensor mass is made up of embryos at various early stages of development. Each embryo contains an embryonal head and suspensor system.

Maintenance of Embryonal Suspensor Masses: The ESM is separated from the original explants and transferred onto solid maintenance medium (DM-2). ESM cultures multiply by natural conifer-type cleavage polyembryony. ESM cultures are subcultured every two weeks onto fresh medium and incubated in the dark at 23° C. The ESM cultures are divided into two pieces when they reach 1 cm long, and all the pieces are maintained until there are several that can be used to start a suspension culture.

Establishing Suspension Cultures: One to two grams (fresh weight) ESM (four or five 1-cm pieces) are transferred into a 250 ml Erlenmeyer flask containing 20 ml of DM-2 liquid medium. The flask is placed on a rotary shaker (90-110 rpm) in darkness at 23° C. After one week 25 ml of fresh medium are added to the flask that is returned to the shaker.

After the second week, the cultures are settled for 15 minutes on a tilted flask holder. The supernatant (spent medium) is removed with an aspirating pipette, and a 5 ml broken-tip pipette is used to measure the settled cell volume (SCV). If the SCV is 2-4 ml, the SCV is returned to the flask and medium is added to achieve a 1:9 ratio of cells to medium (v/v). If the SCV is 5 ml or more, the culture is transferred as described below.

When cultures are sufficiently established to produce 5 ml, or more, of settled cells per week, the ESM is maintained by regular weekly subculture. Subculturing is achieved by settling the cultures for 15 minutes, aspirating the supernatant, and measuring 5 ml of ESM into a flask containing 45 ml of fresh DM-2 maintenance medium. ESM is subcultured at a ratio of 1:9 cells to medium (v/v). If a larger volume of cells is desired, the ESM is split into additional flasks over several weeks, until enough cells are available to use a larger flask. Cultures at this stage may be cryostored, or they may be singulated and developed for germination.

Somatic Embryo Singulation: Abscisic acid (ABA) is important for cotyledonary embryo development because it inhibits cleavage polyembryony and allows embryo singulation and further embryo development. ESM suspension cultures are transferred into DM-3 liquid medium containing 10.0 mg/L ABA. After one week, the cultures are subcultured again into DM-3 medium that includes 5.0 mg/L ABA. After another week the cultures are again subcultured into DM-3 medium that includes 5.0 mg/L ABA.

Embryo Development: Embryo development is completed using a liquid development medium, DM-4, that is soaked into a double layer of Concert 10% CC pads in a petri dish or Cambro box. The 2"×2: pads take 15-20 ml of media per pad. The cultures are settled after culture in singulation medium, and aspirated to remove the supernatant. The settled cell volume is measured with a pipette during transfer to a cytostir beaker. A volume of the reserved supernatant, equal to half the settled cell volume, is added to the cytostir beaker, and the culture is then stirred on a stir plate. 0.75 mi settled ESM mixture (approximately 100 mg ESMs) is pipetted onto the filter paper located on DM-4 media-soaked pads. The plates are sealed with two layers of Parafilm, and incubated in the dark at 23° C. After about 7-8 weeks, the ESM cultures produce cotyledonary embryos.

Stratification: Stratification is the process of placing embryos in a cold moist environment for several weeks, which is thought to simulate winter.

Plates are prepared that include a single layer of pad material (2"×2" 10% CC., or larger cut to fit Cambro boxes). About 18-19 ml liquid SM medium are added per 2"×2" pad (more for boxes). A filter paper bearing the Douglas fir embryos is transferred from development plates to pads of stratification medium. Plates are sealed with parafilm and placed in the dark at 2-6° C. for four weeks. After stratification, the mature somatic embryos are removed from plates and may be inserted into manufactured seed for subsequent germination and seedling establishment, or may be directly germinated.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for producing conifer cotyledonary somatic embryos, the method comprising the step of culturing embryogenic conifer tissue in, or on, a development medium comprising abscisic acid at a concentration in the range of from about 1 mg/L to about 200 mg/L for a period of time sufficient to produce conifer cotyledonary somatic embryos from the embryogenic conifer tissue, wherein the volume of development medium is in the range of from about 35 ml to about 50 ml per 0.5 mL of embryogenic conifer tissue.

2. The method of claim 1, wherein the embryogenic conifer tissue consists essentially of embryonal suspensor masses.

3. The method of claim 1, wherein the embryogenic conifer tissue is from a conifer of the genus *Pinus*.

4. The method of claim 3, wherein the embryogenic conifer tissue is Loblolly pine embryogenic tissue.

5. The method of claim 4, wherein the embryogenic conifer tissue consists essentially of embryogenic suspensor masses.

6. The method of claim 1, wherein the embryogenic conifer tissue is from a conifer of the genus *Pseudotsuga*.

7. The method of claim 6, wherein the embryogenic conifer tissue is from Douglas fir.

8. The method of claim 7, wherein the embryogenic conifer tissue consists essentially of embryonal suspensor masses.

9. The method of claim 1, wherein the development medium is a liquid development medium.

10. The method of claim 1, wherein the development medium is a solid development medium.

11. The method of claim 1, wherein the embryogenic conifer tissue is cultured in, or on, the development medium for a period of from about six weeks to about 14 weeks.

12. The method of claim 1, wherein the osmolality of the development medium is from about 250 mM/Kg to about 450 mM/Kg.

13. A method for producing Douglas fir cotyledonary somatic embryos, the method comprising the steps of:
  (a) culturing Douglas fir zygotic embryos in, or on, an initiation medium for a period of time sufficient to produce embryonal suspensor masses;
  (b) culturing the embryonal suspensor masses in, or on, a maintenance medium under conditions effective to promote multiplication of the embryonal suspensor masses; and
  (c) culturing the multiplied embryonal suspensor masses in, or on, a development medium comprising abscisic acid at a concentration in the range of from about 1 mg/L to about 200 mg/L for a period of time sufficient to produce Douglas fir cotyledonary somatic embryos from the embryonal suspensor masses, wherein the volume of development medium is in the range of from about 35 ml to about 50 ml per 0.5 mL of embryogenic conifer tissue.

14. A method for producing Loblolly pine cotyledonary somatic embryos, the method comprising the steps of:
  (a) culturing Loblolly pine zygotic embryos in, or on, an initiation medium for a period of time sufficient to produce embryonal suspensor masses;
  (b) culturing the embryonal suspensor masses in, or on, a maintenance medium under conditions effective to promote the multiplication of the embryonal suspensor masses; and
  (c) culturing the multiplied embryonal suspensor masses in, or on, a development medium comprising abscisic acid at a concentration in the range of from about 1 mg/L to about 200 mg/L for a period of time sufficient to produce Loblolly pine cotyledonary somatic embryos from the embryonal suspensor masses, wherein the volume of development medium is in the range of from about 35 ml to about 50 ml per 0.5 mL of embryogenic conifer tissue.

* * * * *